United States Patent
Kreuter et al.

(12)

(10) Patent No.: US 6,207,164 B1
(45) Date of Patent: *Mar. 27, 2001

(54) PROCESS FOR THE PREPARATION OF A STABLE, HOMOGENEOUS, EXTRACT FREE OR NEARLY FREE FROM SECONDARY REACTION PRODUCTS

(75) Inventors: Matthias-H. Kreuter, Walenstadt (DE); Rudolf Steiner, Bäch (CH)

(73) Assignee: Emil Flachsmann AG (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/922,398

(22) Filed: Sep. 3, 1997

(30) Foreign Application Priority Data

Sep. 3, 1996 (SE) ........................................ 216696

(51) Int. Cl.⁷ ..................................................... A61K 35/78
(52) U.S. Cl. ............................................................ 424/195.1
(58) Field of Search ........................................... 424/195.1

(56) References Cited

U.S. PATENT DOCUMENTS

| | | | |
|---|---|---|---|
| 3,872,227 | * 3/1975 | Hoff et al. | 514/198 |
| 5,176,913 | * 1/1993 | Honerlagen et al. | 424/195.1 |
| 5,401,502 | * 3/1995 | Wunderlich et al. | 424/195.1 |
| 5,405,616 | * 4/1995 | Wunderlich et al. | 424/451 |
| 5,683,722 | * 11/1997 | Derrieu et al. | 424/493 |

FOREIGN PATENT DOCUMENTS

| | | |
|---|---|---|
| 19542331 | * 5/1997 | (DE). |
| 347493 | 12/1989 | (EP). |
| 664131 | * 7/1995 | (EP). |
| 702957 | * 3/1996 | (EP). |
| 62-036329 | * 2/1987 | (JP). |

OTHER PUBLICATIONS

"Remington: The Science and Practice of Pharmacy", vol. II (1995) (Mack Publishing: Easton PA), p. 1651–21, 1642–49.*

Database WPI, Week 8551, Derwent Publications, Nov. 1985.

Database WPI, Week 9208, Derwent Publications, Jan. 1992.

Database WPI, Week 9139, Derwent Publications, Aug. 1991.

Database WPI, Week 9128, Derwent Publications, Jun. 1991.

Database WPI, Week 7711, Derwent Publications, Sep. 1976.

* cited by examiner

*Primary Examiner*—Christopher Tate
(74) *Attorney, Agent, or Firm*—Burns, Doane, Swecker & Mathis, LLP

(57) ABSTRACT

A process for the preparation of a stable, homogenous extract of plants or plant parts is disclosed. The process comprises mixing and extracting the plants or plant parts charged in a fresh and/or dried state with at least one solvent and at least one agent (having various disclosed properties), then filtering insoluble compounds to obtain a filtrate which is substantially free of secondary reaction products and contains a native compound mixture. The filtrate is concentrated to a spissum extract and the pressure used for the concentration is adjusted according to the vapor pressure of the solvent(s).

68 Claims, No Drawings

PROCESS FOR THE PREPARATION OF A STABLE, HOMOGENEOUS, EXTRACT FREE OR NEARLY FREE FROM SECONDARY REACTION PRODUCTS

The present invention is directed to a process for the preparation of a stable, homogenous extract free or nearly free, from secondary reaction products, which contains the respective desired genuine substance mixture in a complete or nearly complete form, whereby this extract is obtained from plants or parts thereof, which may be charged in a fresh and/or dried state in treated or untreated form.

This invention is also directed to a means for carrying out this process.

This invention is also directed to a stable, homogeneous extract free or nearly free, from secondary reaction products which is obtained from plants or parts thereof.

Usually plant extracts are prepared through extraction with alcohols, mixtures of water and alcohols or also only with water.

When such a plant extract shall be transferred into a viscous form, a so called spissum extract, or into a dry form, a so called siccum extract, then the present solvent or mixture of solvents must be removed partially or completely.

This is usually done under evaporation of the solvent(s) under reduced pressure and at elevated temperatures.

These processes are described in pharmacopeias, for example in "Deutsches Arzneibuch" (DAB) or in "Europäisches Arzneibuch" (EuAB).

When for example *Chelidonium majus L.* is extracted according to such a process and is then concentrated and dried, then are observed decomposition and polymerisation processes as well as a sedimentation and a flotation of the contents compounds.

As a consequence thereof the resulting product represents not an equivalent preparation with regard to the used amount of the plant, because the so obtained substance mixture does not correspond with the genuine substance mixture, dissolved from the plant.

When for example *Melilotus officinalis L. Lam. em. Thuill.* is extracted according to an above mentioned process and is then concentrated and dried, then is noted a loss of volatile components, such as cumarins.

As a consequence thereof also this resulting product represents not an equivalent preparation with regard to the used amount of the plant, because the so obtained substance mixture does not correspond with the genuine substance mixture, dissolved from the plant.

When for example *Hypericum perforatum L.* is extracted according to an above mentioned process, what is usually done in a ratio from the plant to the used solvent from 1:1 to 1:20, especially 1:10, then the hardly soluble portions, such as the dianthrones, are extracted incompletely from the plant.

As a consequence thereof also this resulting product represents not an equivalent preparation with regard to the used amount of the plant, because the so obtained substance mixture does not correspond with the from the plant extractable geniune substance mixture.

When for example *Allium sativum L.* is extracted according to an above mentioned process and is then concentrated and dried, then are observed during the whole process chemical and/or enzymatic reactions between one or more in the extract contained substance(s).

These reactions are nearly completely prevented with the process described in EP 0 347 493.

The product obtained according to this process has at an elevated temperature, that is a temperature of 25° C. and more, an insufficient stability of the thiosulfinates, for example alliin.

Such products obtained according to EP 347 493 which have been stored during a longer time, for example one month, at a temperature of more than 25° C. represent thus no longer an equivalent preparation with regard to the geniune substance mixture dissolved from the plant.

When a tanning agents and/or isoprenoides containing plant extract is transferred into an encapsulable mass according to EP 0 496 705, then at the use of polyethylene glycol sequences containing carrier materials, such as polethylene glycols, polysorbates, are observed sedimentations, flotations, inhomogeneities and chemical reactions during or after the preparation of such masses.

It has been noted that plant extracts, which contain tanning agents and/or isoprenoides, react during the encapsulation into a gelatin capsule with the gelatin envelope, and thus may influence the elasticity of the capsule envelope and its dissolving behaviour in the stomach or in the intestine.

This drawback have the products described in EP 0 464 274 A1 and EP 0 496 705.

This behaviour of tanning agents is utilized for example in the preparation of leather and is known since hundreds of years.

This behaviour of certain isoprenoides, especially the aldehydo derivatives of monoterpenes and sesquiterpenes, especially their reactivity with amino groups containing compounds, is also generally known and is utilized with intention for the preparation of derivatised soft gelatin capsules with retarded dissolving behaviour; see DAB 10, comment K 20.

According to DE PS 44 34 170 the object consists therein to provide peroral applicable extracts of *Hypericum perforatum L.,* which have a higher release ratio with regard to conventional preparations, that is a higher bioavailability of the active components in the stomach-intestine tract.

This is ostensibly reached in that the non-volatile phase of the extract is bonded to polyvinylpyrrolidone in micro disperse form and/or in the form of a solid solution.

It is asserted in DE PS 44 34 170 that the plurality of active components shall be bonded to polyvinylpyrrolidone.

This assertion is sustained on the measurement of the liberation of the dianthrones from the extract according to the prescriptions of DAB 10 V.5.4.

But according to the examples of DE PS 44 34 170 the extract is composed only of about 0.03% (0.1 mg) dianthrones and about 99.97% (289.9 mg) of not explicitely mentioned further active components, accompanying substances and polyvinylpyrrolidone.

Experimental statements for the bioavailability of the other about 99% of the further active components and accompanying substances are not given.

Thus, no experimental proof for the above assertion is given.

The process described in DE PS 44 34 170 is up to the receipt of the fluid extract an already above mentioned known conventional process with which no complete extraction of the active components is obtained.

The polyvinylpyrrolidone is exclusively added to this fluid extract.

In EP 0 599 307 A1 is also described a conventional process for the preparation of a fluid extract of *Hypericum perforatum L.*

The in this fluid extract contained dianthrones are removed selectively by the addition of polyvinylpyrrolidone by means of precipitation and filtration from this fluid extract.

In the so obtained nearly dianthrone-free product are identified experimentally further active components.

Thus, there exists a contradiction between the statements contained in DE PS 44 34 170 and EP 0 599 307 A1.

In JP-A-60 222 412 is described a process for the separation of insoluble substances which are contained in aqueous liquid medicaments.

These medicaments contain plant components.

According to this document crude medicament substances on the basis of plant extracts may contain insoluble micro particles which often may be separated only hardly with usual filtration methods, and which may cause turbidities and precipitations.

According to this document, it has been found that crude medicament substances extracted from some plants may form white turbidities together with polyvinylpyrrolidone.

But when before the addition of polyvinylpyrrolidone a with polyoxyethylene hardened caster-oil derivative is added, then substances aggregate and easily form precipitates, which may be separated in an easy way.

This means that according to this document such substances are previously removed which form turbidities and precipitations. The aggregate-like precipitations are not further described.

The starting material is always an already prepared plant extract.

Thus, according to this document the undesired formation of precipitates has been optimized through previous addition of a polyoxyethylene hardened caster-oil derivative, which leads to aggregate-like and thus better separatable precipitates.

It is an object of the present invention to provide extracts from plants or parts thereof and these extracts containing pharmaceutical acceptable administrative forms, whereby these extracts shall contain the respective desired geniune substance mixture in a complete or nearly complete form.

These extracts and administrative forms shall be stable and homogeneous, and shall fullfill especially the corresponding in the international ICH-guideline contained rules.

These extracts and administrative forms shall have in contrary to conventional products a considerably reduced or no content of secondary reaction products.

These extracts and administrative forms shall be prepared by means of a simple and economical process.

It has been found quite surprisingly that the above mentioned objects are reached when during or after the extraction of the plant or a part thereof an agent A is added.

In the inventive process are used as agent A preferably protein hydrolysates and/or polyvinylpyrrolidones.

The extract of *Allium sativum L.* is prepared preferably up to the receipt of the fluid extract according to the process as described in EP 0 347 493.

It has been determined that the addition of an agent A, for example Kollidon K 25 (BASF), to this fluid extract, followed by the following further processing to a dry extract, results in a product, which has a significantly reduces sensitivity against elevated temperatures.

When conventional garlic preparations are stored at elevated temperatures then are observed—as already mentioned above—already at temperatures of more than 25° C. losses of active substances.

These losses are not observed even at a temperature of 30° C. with an inventive garlic preparation.

This stability improvement is a big process in a twofold manner.

Thus, on one hand expenditures during transportation and at the storage are reduced, and on the other hand the safety of the medicament is increased.

It has been determined that the addition of an agent A, for example Kollidon 17 PF (BASF), to a mainly water soluble compounds containing fluid extract of *Melilotus officinalis L. Lam. em. Thuill.,* followed by the following further processing to a dry extract, results in a product, which has a significantly increased content of cumarins.

This is explained by the fact that the normally during the evaporation of the water/ethanol mixture volatile cumarins are retained obviously through an interaction with the agent A and thus remain in the residue.

This is a big process because it was not yet possible to concentrate aqueous/ethanolic, cumarins containing solutions without the loss of the cumarins in an economical way.

Of special meaning are inventive extracts of Melilotus, because they are much more suitable for the preparation of injectable preparations than conventional products, because they contain the desired watersoluble active compounds and no waxes, chlorphyll and further hardly watersoluble compounds/residues.

Conventional cumarins containing extracts are only available by using highly lipophilic, waterfree or nearly waterfree solvents.

Therefore, conventional extracts contain less of the desired watersoluble active compounds and in return more for the activity and for the use troublesome and undesired compounds.

It has been determined that the addition of an agent A, for example Kollidon K 90 (BASF), to a fluid extract of *Chelidonium majus L.,* followed by the following further processing to a dry extract, results in a product, which has a significantly increased content of alkaloids as well as a homogeneity.

This high content of alkaloids is explained by the fact, that obviously through an interaction between the alkaloids and the agent A the decomposition processes are prevented which are observed in conventionally prepared products.

The homogeneity of this inventive extract may be explained by the fact that obviously through an interaction between the agent A and the isoprenoids a polymerisation of the latter to latex and/or latex-like compounds does not take place, and thus no phase separation occurs.

Not only are conventional preparations increased with regard to the content of alkaloids, but also the homogeneity of the product is increased.

The avoidance of the decomposition of the alkaloids has a special meaning because all important chelidoniumalkaloids contain methylene dioxy groups, which during the decomposition reactions may be cleaved as formaldehyde.

It can not be excluded that in such products the decomposition products are of toxic nature.

It has been determined that the addition of an agent A, for example Gelita-Sol D (DGF Stoess) during the preparation of the fluid extract of Herba Hyperici (*Hypericum performatum L.*), the amount of the extractable dianthron compounds is significantly increased.

This may be explained by the fact that the solubility product of the in mixtures of water and ethanol only hardest soluble dianthrons, obviously through interaction with the agent A, is significantly increased.

Thereby is obtained a more complete extraction of the plant, what is a progress with regard to conventional extraction processes.

A pharmaceutical preparation having a high content of dianthrones may be important for the effect at depressive emotional deterioration states, which are associated with viral illnesses, because the dianthrons have antiviral properties.

The following examples shall illustrate the present invention.

EXAMPLE 1

400 kg of Herba Chelidonii (*Chelidonium majus L.*) with a measured total alkaloid content of 1.0% by weight were mixed in a dried and cut form (cut size 1 to 3 cm) with 3200 kg of a mixture of 7 parts by weight of ethanol and 3 parts by weight of water.

This mixture was stirred in a container with cut-, stir-, heating- and cooling-devices at room temperature during 30 minutes under further cutting to small pieces of the plant parts.

Then was heated to a temperature between 60° C. and 70° C. At this temperature was extracted under stirring during 2 hours.

Then was filtered. To the obtained filtrate were added 15 kg of Kollidon K 90 (BASF) and were dissolved under stirring at a temperature between 40° C. and 50° C.

The so obtained solution was concentrated at a pressure between 50 mbar and 100 mbar at a temperature between 40° C. and 50° C. up to a dry substance content of 40% by weight.

There were obtained 220 kg of spissum extract having a measured total alkaloid content (DAB) of 1.82% by weight.

This content corresponds to a 100% yield of alkaloids.

EXAMPLE 2

220 kg of the spissum extract obtained according to example 1 were mixed homogeneously with 12 kg of precipitated silicic acid (DAB).

This mixture was dried at a pressure between 20 mbar and 30 mbar and a maximum product temperature of 40° C. during 90 minutes.

The so obtained dry extract was sieved and mixed homogeneously.

There were obtained 100 kg of dry extract having a measured total alkaloid content (DAB) of 3.93% by weight.

This content corresponds to a 98% yield of alkaloids.

EXAMPLE 3

According to the example 1 there were processed 4 kg of Herba Chelidonii, 32 kg of a mixture of 7 parts by weight of ethanol and 3 parts by weight of water as well as 0.15 kg of Kollidon K 90.

In the obtained spissum extract (2.0 kg) was measured a total alkaloid content (DAB) of 2.0% by weight.

This content corresponds to a 100% yield of alkaloids.

2.0 kg of this spissum extract were mixed homogeneously with 120 g of precipitated silicic acid (DAB) and were processed according to example 2.

In the obtained dry extract (1 kg) was measured a total alkaloid content (DAB) of 4.08% by weight.

This content corresponds to a 102% yield of alkaloids.

It is known to somebody skilled in the art that in the used measuring method due to the accuracy of measurement values of more than 100% may occur.

EXAMPLE 4 (comparative example)

According to the example 1 there were processed 4 kg of Herba Chelidonii and 32 kg of a mixture of 7 parts by weight of ethanol and 3 parts by weight of water without the addition of Kollidon K 90.

In the obtained spissum extract (1.5 kg) was measured a total alkaloid content (DAB) of 1.7% by weight.

This content corresponds to a 64% yield of alkaloids.

1.5 kg of this spissum extract were mixed homogeneously with 120 g of precipitated silicic acid (DAB) and were processed according to example 2.

In the obtained dry extract (0.66 kg) was measured a total alkaloid content (DAB) of 2.3% by weight.

This content corresponds to a 57.5% yield of alkaloids.

In the following tables 1 and 2 are summarized several datas.

TABLE 1

|  | Example 3 (spissum extract) | Example 4 (spissum extract) |
| --- | --- | --- |
| Yield (measured as dry substance and referred to the amount of the used plant) | 17.5% *) | 11% |
| Yield of alkaloids | 100% | 64% |
| Viscosity (Pa.s, 25° C.) | 3.0 | 1.0 to 50.0 **) |
| Sedimentation | no | yes |
| Flotation | no | yes |
| Homogeneity | yes | no |

*)without Kollidon K 90
**)inhomogeneous, multiphase mixture

TABLE 2

|  | Example 3 (dry extract) | Example 4 (dry extract) |
| --- | --- | --- |
| Yield (measured as dry substance and rererred to the amount of the used plant) | 17.5% *) | 11% **) |
| Yiels of alkaloids | 102% | 57.5% |
| Homogeneity | yes | no |
| Sintering point | 71° C. | 43° C. |

*)without Kollidon K 90 and without precipitated silicic acid
**)without precipitated silicic acid

EXAMPLE 5

4 kg of Herba Hypericic (*Hypericum perforatum L.*) with a measured dianthrone content of 0.12% by weight were mixed in a dried and cut form (cut size 1 to 3 cm) with 32 kg of a mixture of 6 parts by weight of ethanol and 4 parts by weight of water.

This mixture was stirred vigorously in a container with cut-, stir-, heating- and cooling-devices at a temperature from 30° C. to 40° C. during 5 minutes under further cutting to small pieces of the plant parts.

Then were added 200 g of Gelita-Sol D (DGF Stoess).

This mixture was extracted at a temperature from 30° C. to 40° C. under stirring during 90 minutes.

Then was filtered. There were obtained 26 kg of a filtrate (fluid extract) having a dry substance content of 3.8% by weight and a dianthrone content (DAC) of 0.46% by weight, referred to the dry substance.

This corresponds to a 96% yield of dianthrone.

This filtrate was concentrated at a pressure between 50 mbar and 150 mbar at a temperature between 50° C. and 60° C. up to a dry substance content of 60% by weight.

There were obtained 1.65 kg of a spissum extract having a measured dianthrone content (DAC) of 0.45% by weight, referred to the dry substance.

This corresponds to a 94% yield of dianthrone.

EXAMPLE 6

1.65 kg of the spissum extract, obtained according to example 5, were mixed with 50 g of an aqueous, 40% by weight of gummi arabicum (DAB) containing solution.

This mixture was spray dried under the addition of 20 g highly disperse silicon dioxide (DAB).

The so obtained dry extract was sieved and mixed homogeneously.

There was obtained 1 kg of a dry extract having a measured dianthrone content (DAC) of 0.47% by weight.

This content corresponds to a 98% yield of dianthrones.

It is known to somebody skilled in the art that in the used measuring method due to the accuracy of measurement higher values than methematically expected may occur.

EXAMPLE 7 (comparative example)

According to the example 5 there were processed 4 kg of Herba Hypericic and 32 kg of a mixture of 6 parts by weight of ethanol and 4 parts by weight of water without the addition of Gelita-Sol D.

In the obtained fluid extract (26.3 kg) having a dry substance content of 3.1% by weight was measured a dianthrone content (DAC) of 0.34% by weight, referred to the dry substance.

This content corresponds to a 71% yield of dianthrones.

This fluid extract was concentrated according to example 5 to a spissum extract.

In the obtained spissum extract (1.4 kg, 60% dry substance) was measured a dianthrone content (DAC) of 0.33% by weight.

This content corresponds to a 69% yield of dianthrones.

1.4 kg of this spissum extract were processed in analogy to example 6 to a dry extract.

There were obtained 860 kg dry extract having a measured dianthrone content (DAC) of 0.34% by weight.

This content corresponds to a 61% yield of dianthrones.

EXAMPLE 8

4 kg of Herba Meliloti (*Melilotus officinalis L. Lam. em. Thuill.*) having a measured cumarin content of 0.38% by weight (HPLC) were mixed in dried and cut form (cut size 1 to 3 cm) with 60 kg of a mixture of 1 part by weight of ethanol and 3 parts by weight of water.

This mixture was stirred and extracted in a container with cut-, stir-, heating- and cooling-devices at a temperature from 30° C. to 40° C. during 2 hours under further cutting to small pieces of the plant parts.

Then was filtered. To the obtained filtrate (54 kg, dry substance content 1.5% by weight, 1.56% by weight cumarin content, referred to the dried substance) were added 200 g of Kollidon 17 PF (BASF) and were dissolved unter stirring at a temperature between 30° C. and 40° C.

The so obtained solution was concentrated at a pressure between 20 mbar and 30 mbar at a temperature between 30° and 40° C. up to a dry substance content of 30% by weight.

There were obtained 3.3 kg of spissum extract having a measured cumarin content (HPLC) of 1.55% by weight, referred to the dry substance.

This content corresponds to a 99% yield of cumarins.

EXAMPLE 9

3.3 kg of the spissum extract obtained according to example 8 were spray dried.

The so obtained dry extract was sieved and mixed homogeneously.

There was obtained 1 kg of dry extract having a measured cumarin content (HPLC) of 1.48% by weight.

This content corresponds to a 94.9% yield of cumarins.

EXAMPLE 10 (comparative example)

4 kg of Herba Meliloti and 60 kg of a mixture of 1 part by weight of ethanol and 3 parts by weight of water were processed according to example 8 without the addition of Kollidon 17 PF.

In the obtained filtrate were measured the same values as in example 8.

In the obtained spissum extract (2.7 kg) was measured a cumarin content (HPLC) of 0.93% by weight, referred to the dry substance.

This content corresponds to a 48.4% yield of cumarins.

2.7 kg of this spissum extract were processed according to example 9 to a dry extract.

There were obtained 800 g of a dry extract having a measured cumarin content (HPLC) of 0.90% by weight.

This content corresponds to a 46.5% yield of cumarins.

EXAMPLE 11

12 kg of fresh entire *Bulbus Allii sativi* (*Allium sativum L.*) were mixed with 84 kg of a mixture of 9 parts by weight of ethanol and 1 part by weight of water.

This mixture was stirred in a container with cut-, stir-, heating- and cooling-devices at room temperature during 10 minutes under cutting to small pieces of the plant parts.

This mixture was stirred and extracted at room temperature during 80 minutes.

Then was filtered. To the obtained filtrate were added 300 g Kollidon K 25 (BASF) and were dissolved under stirring at room temperature.

The obtained solution was concentrated at a pressure between 30 mbar and 100 mbar and at a temperature between 30° C. and 40° C. up to a dry substance content of 60% by weight.

There were obtained 1.7 kg of spissum extract.

This spissum extract was dried at a pressure between 20 mbar and 30 mbar and a maximum product temperature of 40° C. during 90 minutes.

The so obtained dry extract was sieved and mixed homogeneously.

There was obtained 1 kg of dry extract having a measured alliin content (HPLC) of 9.0% by weight.

EXAMPLE 12 (comparative example)

According to example 11 there were processed 12 kg of fresh entire *Bulbus Allii sativi* and 84 kg of a mixture of 9 parts by weight of ethanol and 1 part by weight of water without the addition of Kollidon K 25.

In the obtained dry extract (700 g) was measured an alliin content (HPLC) of 12.1% by weight.

In the following table 3 are summarized several datas concerning the storage stabilities.

TABLE 3

|  | Example 11 (dry extract) | | | Example 12 (dry extract) | | |
| --- | --- | --- | --- | --- | --- | --- |
| Temperature (° C.) | 20 | 25 | 30 | 20 | 25 | 30 |
| Alliin content (in %, referred to the as 100% defined initial value) | | | | | | |
| at the beginning | 100 | 100 | 100 | 100 | 100 | 100 |
| after 1 month | 100 | 100 | 100 | 100 | 98 | 85 |
| after 3 months | 100 | 100 | 100 | 100 | 97 | 64 |
| after 6 months | 103 | 103 | 98 | 100 | 97 | 31 |
| after 12 months | *) | *) | *) | 98 | 95.7 | 26 |
| after 18 months | *) | *) | *) | 95 | 94 | 13 |
| after 24 months | *) | *) | *) | 94 | 93 | 9 |
| after 36 months | *) | *) | *) | 92 | 92 | 3 |

*)not measured

What is claimed is:

1. A process for the preparation of a stable, homogeneous extract of plants or parts thereof, comprising mixing plants or plant parts charged in a fresh and/or dried state with at least one solvent and at least one agent and extracting the plants or plant parts with the solvent and agent, and thereafter filtering insoluble compounds so as to obtain a filtrate, wherein said filtrate is substantially free of secondary reaction products and contains a native compound mixture;

and wherein said agent:
   (i) increases the solubility of at least one extracted compound contained in the filtrate;
   (ii) increases the viscosity of the filtrate in the presence of the solvent(s);
   (iii) decreases the steam pressure of volatile extracted compounds contained in the filtrate;
   (iv) prevents or reduces the chemical and/or enzymatic reactions between one or more extracted compounds contained in the filtrate;
   (v) prevents or reduces the sedimentation and/or flotation of extracted compounds contained in the filtrate when the filtrate is in liquid or semisolid form or is dissolved and/or suspended and/or emulsified in at least one solvent; and
   (iv) increases the stability and/or homogeneity of at least one extracted compounds contained in the filtrate, wherein said filtrate is concentrated to a spissum extract and the pressure used for the concentration is adjusted according to the vapor pressure of the solvent(s), and optionally the spissum extract is dried to obtain a dry extract which is in a solid state of aggregation at a temperature below 60° C., or the spissum extract is mixed with at least one pharmaceutically acceptable solvent so that a preparation is obtained which is in a liquid state of aggregation at a temperature of below 50° C.

2. The process according to claim 1, wherein said extract is concentrated to a spissum extract at a temperature below 70° C.

3. The process according to claim 1, wherein the spissum extract is dried by means of a vacuum belt device.

4. The process according to claim 1, wherein the pharmaceutically acceptable solvent is selected from the group consisting of water, glycerol, propylene glycol, and polyethylene glycol with an average molecular weight ranging from 300 to 1500.

5. The process according to claim 4, wherein the pharmaceutically acceptable solvent is polyethylene glycol with an average molecular weight of 300.

6. The process according to claim 1, wherein at least one pharmaceutically acceptable additive and/or auxiliary agent is added to the mixture.

7. The process according to claim 6, wherein the pharmaceutically acceptable additive and/or auxiliary agent is added to said extract prior to drying or mixing with a pharmaceutically acceptable solvent.

8. The process according to claim 6, wherein the pharmaceutically acceptable additive and/or auxiliary agent is selected from the group consisting of emulsifiers, stabilizers, antioxidants, dyestuffs, aromas, disintegration agents, agents which increase melting point, and agents which reduce hygroscopicity.

9. The process according to claim 1, wherein said extract is mixed with at least one carrier material for said extract, wherein said carrier material is encapsulatable and is inert against substances contained in the mixture, and the so obtained mixture is freed partially or completely from the solvent or mixture of solvents.

10. The process according to claim 9, wherein the carrier material is selected from the group consisting of polyethylene glycol with an average molecular weight ranging from 300 to 600, fatty acid esters of polyglycerines, lecithins, silicone oils, sorbitan fatty acid esters, sorbates of fatty acids, polysorbates of fatty acids, waxes, polyglycerines, triglycerides, fatty acids, fatty oils, paraffins, and mixtures thereof.

11. The process according to claim 10, wherein the carrier material is polyethylene glycol with an average molecular weight of 300.

12. The process according to claim 9, wherein water and/or glycerol and/or propylene glycol is added to said so obtained mixture in an amount of 5% by weight to 20% by weight of the end product.

13. The process according to claim 12, wherein water and/or glycerol and/or propylene glycol is added to said so obtained mixture in an amount of 12% by weight to 15% by weight of the end product.

14. The process according to claim 1, wherein said plants are food plants, medical plants or spice plants.

15. The process according to claim 14, wherein said plants are selected from the group consisting of Allium-species, *Ammi visnaga L., Arctostaphylos uva-ursi Spreng., Arnica montan L., Artemisia absinthium L., Asparagus officinalis L.*, Aspidosperma-species, Astragalus-species, *Atropa belladonna L., Avena sativa L., Berberis vulgaris L.,* Betula-species, *Brassica nigra L., Koch, Calendula officinalis L., Camellia sinensis L., Capsicum frutescens L., Carum carvi L., Chelidonium majus L., Chysanthemum parthenium, Chrysanthemum vulgare Asch., Cimicifuga racemosa L.,* Cinnamonum-species, Citrus-species, *Centella asiatica L.,* Crategus-species, *Cucurbita pepo L.,* Curcuma-species, *Cytisus scoparius L.,* Drosera-species, *Echinacea angustifolia D.C., Enchinacea pallida Nutt., Enchinacea purpurea L. Moench, Elettaria cardamomum L.* White et Mathon, Ephedra species, *Equisetum arvense L., Eucalyptus globulus Labill., Euphrasia offic. L., Foeniculum vulgare Miller,* Fragaria species, *Fumaria officinalis L., Galium odoratum L., Gaultheria procumbens L., Ginkgo biloba L., Glycine max. L., Hamamelis virginia L., Haronga madagascariensis* (Chois), *Hedeoma pulegioides L. Pers., Herniaria glabra L., Humulus lupulus L., Hypericum perforatum L., Hysopus officinalis L., Ilex paraguariensis St. Hil., Illicium verum Hook. F., Iluna helenium L., Iris pallida Lam., Jasminum*

*grandiflorum L., Laurus nobilis L.,* Lavandula species, *Lawsonia inermis L., Levisticum officinale Koch, Marsdenia cundurango* (Reichenback), *Matricaria chamomilla L., Melilotus officinalis L. Lam.em. Thuill.,* Mentha-species and their varieties, *Myrtus communis L., Ocimum basilica L., Olea europaea L., Ononis spinosa L.,* Origanum-species, *Orthosiphon stamineus Benth., Panax ginseng Meyer, Pausinylstalia yohimba Pierre, Petroselinum crispum* (Mill.) Nym., *Peumus boldus* (Molina), *Phaseolus vulgaris L., Pimenta dioica L. Merill, Pimpinella anisum L., Piper methysticum Forster, Plantago lanceolata L., Potentilla anserina L., Prunus laurocerasus L.,* Rauvolfia-species, *Rosmarinus officinalis L.,* and their subspecies, *Rubus fructicosus L., Ruta graveolens L.,* Salix species, Salvia-species, *Sanguinaria canadensis L., Sarothamnus scoparius L.* Wimmer, *Schisandra chinensis Baill.,* Scopolia-species, *Solidago serotina Ait., Solidago virguarea L.,* Smilax-species, *Sylibum marianum L. Gaertner,* Tabebuia-species, *Taraxacum officinale Web., Thymus serpyllum L., Thymus vulgaris L., Tilia cordata Mill., Tilia playphyllos Scop., Uncaria tomentosa* (Wild), *Urtica dioica L., Valeriana officinalis L.* and their varieties, *Vitex agnus castus L.,* and *Zingiber officinale Roscoe.*

16. The process according to claim 15, wherein said plant is selected from the group consisting of *Allium cepa L., Allium ursinum L., Allium sativum L.:* Bulbus, *Droscera rotundifolia L., Drosera ramentacea Burch, Drosera peltate, Ephedra sinica* (Staph), *Fragaria vesca L., Lavandula officinalis L.,* and Salix alba L.

17. The process according to claim 1, wherein the solvent for preparation of the plant extract is a polar solvent.

18. The process according to claim 17, wherein said polar solvent is selected from the group consisting of water, alcohols, ketones, esters, and mixtures thereof.

19. The process according to claim 18, wherein said alcohol is a $C_1$ to $C_4$ alcohol.

20. The process according to claim 18, wherein said alcohol is ethanol, glycerol or propylene glycol.

21. The process according to claim 18, wherein said ketone is a $C_3$ to $C_5$ ketone.

22. The process according to claim 18, wherein said ketone is acetone.

23. The process according to claim 18, wherein said ester is an alkyl acetate.

24. The process according to claim 23, wherein the alkyl group of said alkyl acetate has 1 to 4 C-atoms.

25. The process according to claim 18, wherein said polar solvent is a mixture of water and ethanol.

26. The process according to claim 1, wherein said agent is a polymeric compound.

27. The process according to claim 26, wherein said polymeric compound is selected from the group consisting of polyvinylpyrrolidones (PVP), vinylacetate-crotonic acid-copolymers, methacrylic acid-ethylacrylate-copolymers, polyethylene glycols with an average molecular weight ranging from 4,000 to 35,000 blockcopolymers from polyethylene glycols and polypropylene glycols, proteins and protein hydrolysates of proteins of plant and/or animal origin, blockcopolymers of ethylene oxide and propylene oxide, and mixtures thereof.

28. The process according to claim 27, wherein said polymeric compound is polyethylene glycol with an average molecular weight of 35,000.

29. The process according to claim 27, wherein said polymeric compound is gelatin.

30. The process according to claim 1, wherein the weight ratio between the plant and the solvent is from 1:1 to 1:30.

31. The process according to claim 30, wherein the weight ratio between the plant and the solvent is from 1:4 to 1:8.

32. The process according to claim 30, wherein the weight ratio between the plant and the agent is from 5:1 to 120:1, and said agent is polyvinylpyrrolidone.

33. The process according to claim 32, wherein the weight ratio between the plant and the agent is from 10:1 to 50:1, and said agent is a vinylacetate-crotonic acid-coppolymer.

34. The process according to claim 30, wherein the weight ratio between the plant and the agent is from 10:1 to 50:1, and said agent is a methacrylic acid-ethylacrylate-copolymer.

35. The process according to claim 30, wherein the weight ratio between the plant and the agent is from 2:1 to 30:1, and said agent is a polyethylene glycol with an average molecular weight ranging from 4,000 to 35,000.

36. The process according to claim 30, wherein the weight ratio between the plant and the agent is from 2:1 to 50:1, and said agent is a block copolymer of a polyethylene glycol and a polyethylene glycol.

37. The process according to claim 30, wherein the weight ratio between the plant and the agent is from 2:1 to 50:1, and said agent is a protein or protein hydrolysate of proteins of plants and/or of animals.

38. The process according to claim 30, wherein the weight ratio between the plant and the agent is from 2:1 to 50:1, and said agent is a blockcopolymer of ethylene oxide and polylene oxide.

39. The process according to claim 30, wherein the weight ratio between the plant and the solvent is from 1:5 to 1:15.

40. The process according to claim 1, wherein the plant or parts thereof is of the family of the Papaveraceas, the solvent is a water/alcohol mixture, the agent is polyvinylpyrrolidone (PVP), the weight ratio between the plant and PVP is from 10:1 to 60:1, and optionally said extract is concentrated to a spissum extract having a water content from 55% by weight to 75% by weight referred to the spissum extract, an agent which increases melting point is added to the spissum extract, and thereafter the spissum extract is dried.

41. The process according to claim 40, wherein the plant or parts thereof of the family of the Papaveraceas is *Chelidonium majus L., Fumaria officinalis L.* or *Sanguinaria canadensis L.*

42. The process according to claim 40, wherein the water/alcohol mixture is a mixture of water and ethanol.

43. The process according to claim 40, wherein the PVP has an average molecular weight ranging from 1,000,000 to 1,500,000.

44. The process according to claim 40, wherein the extract is concentrated to the spissum extract at a temperature below 70° C. and a pressure less than 200 mbar.

45. The process according to claim 40, wherein the agent which increases melting point is silicic acid.

46. The process according to claim 45, wherein the silicic acid is precipitated silicic acid.

47. The process according to claim 1, wherein the plant or parts thereof is of the family of Fabaceas, the solvent is a water/alcohol mixture, the agent is polyvinylpyrrolidone (PVP), the weight ratio between the plant and PVP is from 10:1 to 40:1, and optionally said extract is concentrated to a spissum extract having a water content from 40% by weight to 70% by weight referred to the spissum extract, and thereafter the spissum extract is dried.

48. The process according to claim 47, wherein the plant or parts thereof of the family of Fabaceus is *Melilotus ollicinalis L. Lam. Em. Thuill., Phaseolus vulgaris L.* or Astragalus-species.

49. The process according to claim 47, wherein the water/alcohol mixture is a mixture of water and ethanol.

50. The process according to claim 47, wherein the PVP has an average molecular weight ranging from 2,000 to 54,000.

51. The process according to claim 50, wherein the PVP has an average molecular weight ranging from 7,000 to 11,000.

52. The process according to claim 47, wherein the extract is concentrated to the spissum extract at a temperature below 50° C. and a pressure less than 80 mbar.

53. The process according to claim 52, wherein the extract is concentrated to the spissum extract at a temperature from 30° C. to 40° C. and a pressure less than 50 mbar.

54. The process according to claim , wherein the plant or parts thereof is of the family of the Liliaceas, the solvent is a water/alcohol mixture, the agent is polyvinylpyrrolidone (PVP), the weight ratio between the plant and PVP is from 20:1 to 120:1, optionally said extract is concentrated to a spissum extract having a water content from 30% by weight to 60% by weight referred to the spissum extract, optionally an antioxidant is added to the spissum extract, and thereafter the spissum extract is dried.

55. The process according to claim 54, wherein the plant or parts thereof of the family of Liliaceas are Allium-species.

56. The process according to claim 55, wherein the plant or parts thereof of the family of the Liliaceas is *Allium cepa L., Allium ursinum L.,* or *Allium satirum L.: Bulbus.*

57. The process according to claim 54, wherein the water/alcohol mixture is a mixture of water and ethanol.

58. The process according to claim 54, wherein the PVP has an average molecular weight ranging from 2,000 to 54,000.

59. The process according to claim 58, wherein the PVP has an average molecular weight ranging from 28,000 to 34,000.

60. The process according to claim 54, wherein the weight ratio between the plant and PVP is 90:1.

61. The process according to claim 54, wherein the extract is concentrated to the spissum extract at a temperature below 70° C. and a pressure less than 200 mbar.

62. The process according to claim 54, wherein the antioxidant is α-tocopherol.

63. The process according to claim 1, wherein the plant or parts thereof is of the family of Hypericaceas, the solvent is a water/alcohol mixture, the agent is gelatin, the weight ratio between the plant and gelatin is from 5:1 to 50:1, and optionally said extract is concentrated to a spissum extract having a water content from 30% by weight to 70% by weight referred to the spissum extract, and thereafter the spissum extract is dried.

64. The process according to claim 63, wherein the plant or parts thereof of the family of the Hypericaceas is *Hypericum perforatum L.*

65. The process according to claim 63, wherein the water/alcohol mixture is a mixture of water and ethanol.

66. The process according to claim 63, wherein the gelatin is a partial hydrolysate of gelatin with a viscosity of 22 mPa.s measured as a 35% solution in water at a temperature of 25° C.

67. The process according to claim 63, wherein the weight ratio between plant and gelatin is from 8:1 to 12:1.

68. The process according to claim 63, wherein extract is concentrated to the spissum extract at a temperature below 70° C. and a pressure less than 200 mbar.

* * * * *